United States Patent
Shiga et al.

(10) Patent No.: US 10,521,893 B2
(45) Date of Patent: Dec. 31, 2019

(54) IMAGE PROCESSING APPARATUS, IMAGING SYSTEM AND IMAGE PROCESSING METHOD

(71) Applicant: CANON KABUSHIKI KAISHA, Tokyo (JP)

(72) Inventors: Toshiki Shiga, Yokohama (JP); Toru Sasaki, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 65 days.

(21) Appl. No.: 15/571,809

(22) PCT Filed: May 12, 2016

(86) PCT No.: PCT/JP2016/002336
§ 371 (c)(1),
(2) Date: Nov. 3, 2017

(87) PCT Pub. No.: WO2016/189818
PCT Pub. Date: Dec. 1, 2016

(65) Prior Publication Data
US 2019/0005631 A1    Jan. 3, 2019

(30) Foreign Application Priority Data

May 22, 2015 (JP) ................................. 2015-104609
Dec. 22, 2015 (JP) ................................. 2015-249613

(51) Int. Cl.
*H04N 9/47* (2006.01)
*A62B 1/04* (2006.01)
(Continued)

(52) U.S. Cl.
CPC .............. *G06T 5/50* (2013.01); *G01N 21/31* (2013.01); *G06T 5/007* (2013.01); *G06T 5/009* (2013.01);
(Continued)

(58) Field of Classification Search
USPC ......................................... 348/61, 71, 79, 65
See application file for complete search history.

(56) References Cited

U.S. PATENT DOCUMENTS 8,320,996 B2* 11/2012 Panasyuk ............. A61B 5/0059
600/473
2011/0063420 A1* 3/2011 Masuda ..................... G06T 7/97
348/50
(Continued)

FOREIGN PATENT DOCUMENTS

JP    S61-107482 A    5/1986
JP    H07-049269 A    2/1995
(Continued)

OTHER PUBLICATIONS

Nov. 28, 2017 International Preliminary Report on Patentability in International Patent Appln. No. PCT/JP2016/002336.
(Continued)

*Primary Examiner* — Daquan Zhao
(74) *Attorney, Agent, or Firm* — Venable LLP

(57) ABSTRACT

An image processing apparatus includes: an acquisition unit configured to acquire band images of an object, using filters of which transmission center wavelengths are different from each another; a detection unit configured to select a first band image from the band images, and detect a target region that is to be improved with respect to visibility; a selection unit configured to select a second band image, which includes information, originated from a structure of the object, within the target region, from among the band images other than the first band image; and a generation unit configured to generate a spectral image from a band image. The generation unit uses at least a band image that has been captured using a same filter as the second band image, upon generating a spectral image of the object.

15 Claims, 14 Drawing Sheets

(51) Int. Cl.
  *G06T 5/50* (2006.01)
  *G06T 7/90* (2017.01)
  *H04N 5/232* (2006.01)
  *G06T 5/00* (2006.01)
  *G01N 21/31* (2006.01)
  *H04N 9/07* (2006.01)

(52) U.S. Cl.
  CPC ........... *G06T 7/90* (2017.01); *H04N 5/23229* (2013.01); *H04N 9/07* (2013.01); *G06T 2207/10024* (2013.01); *G06T 2207/10056* (2013.01); *G06T 2207/10152* (2013.01); *G06T 2207/20104* (2013.01); *G06T 2207/20221* (2013.01)

(56) References Cited

U.S. PATENT DOCUMENTS

| | | |
|---|---|---|
| 2012/0147232 A1 | 6/2012 | Takayama et al. |
| 2014/0362205 A1 | 12/2014 | Sasaki |
| 2015/0234171 A1 | 8/2015 | Sasaki |
| 2015/0238126 A1* | 8/2015 | Saito ............... A61B 5/742 |
| | | 600/339 |
| 2017/0038576 A1 | 2/2017 | Sasaki |

FOREIGN PATENT DOCUMENTS

| | | |
|---|---|---|
| JP | H10-216080 A | 8/1998 |
| JP | 2004-336657 A | 11/2004 |
| JP | 2004-357910 A | 12/2004 |
| JP | 2007-307202 A | 11/2007 |
| JP | 2009-066301 A | 4/2009 |
| JP | 2009-204408 A | 9/2009 |
| JP | 2010-181833 A | 8/2010 |
| JP | 2010-264276 A | 11/2010 |
| JP | 2010-276442 A | 12/2010 |

OTHER PUBLICATIONS

Sep. 10, 2019 Japanese Official Action in Japanese Patent Appln. No. 2015-249613.

* cited by examiner

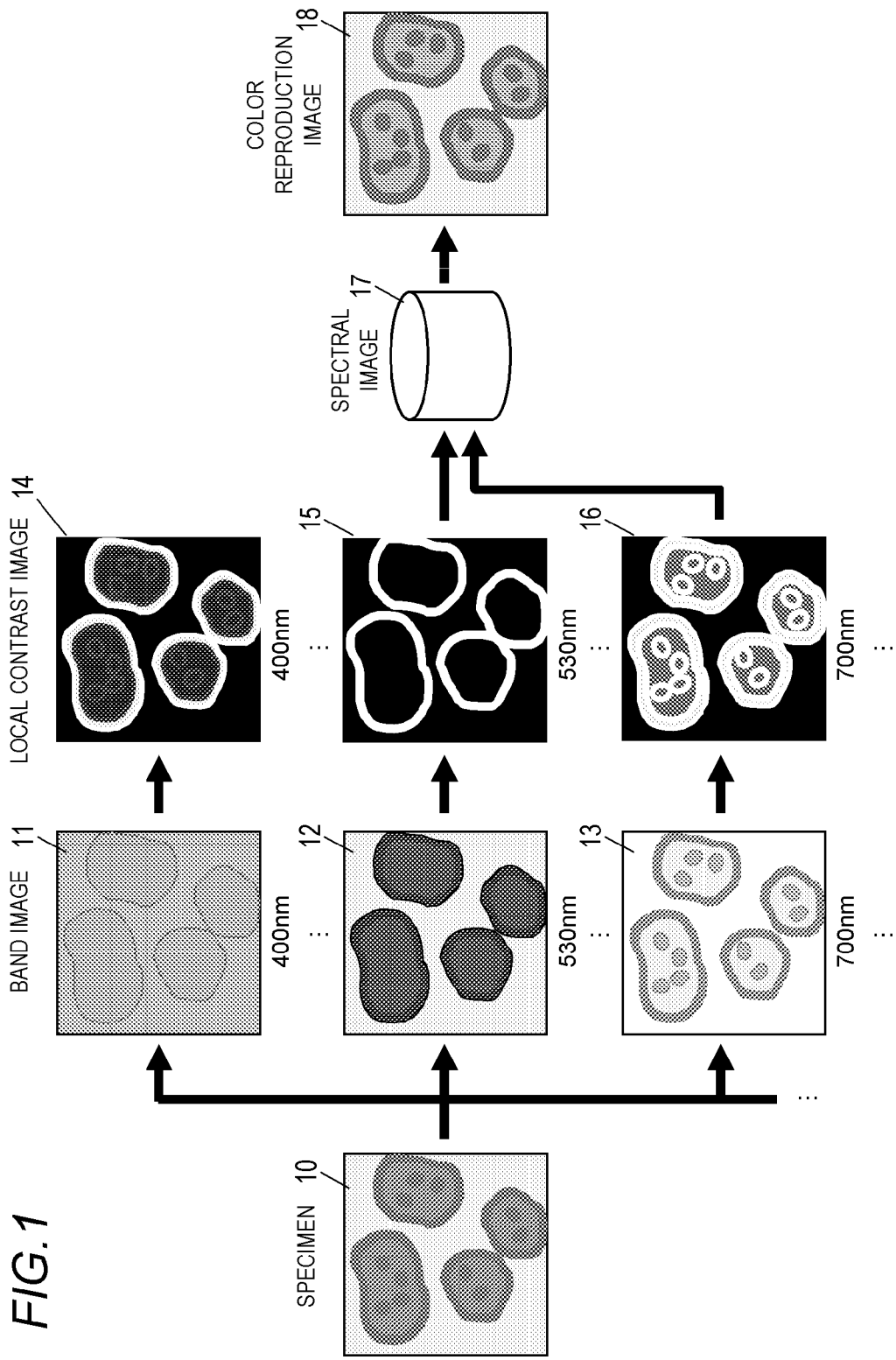

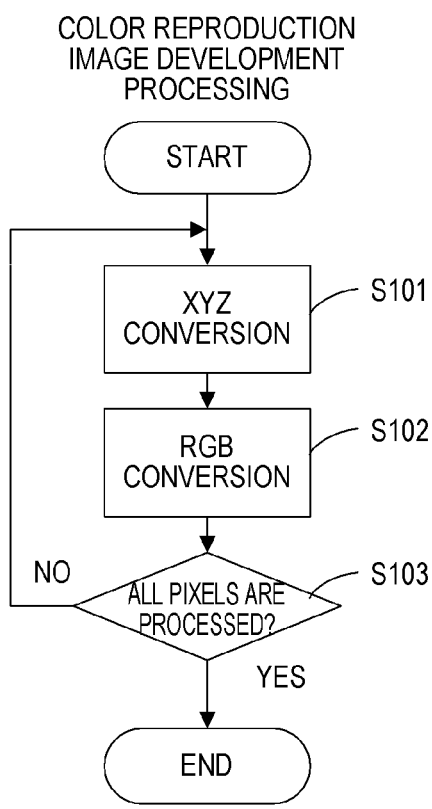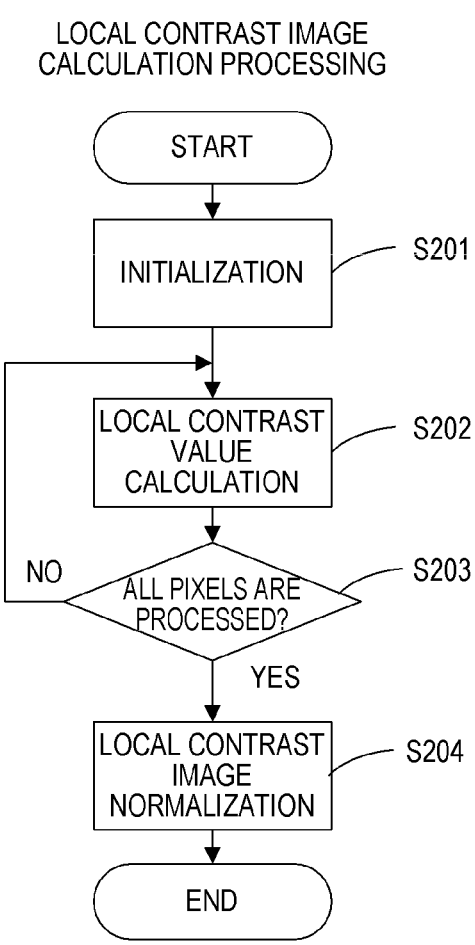

IMAGE PROCESSING APPARATUS, IMAGING SYSTEM AND IMAGE PROCESSING METHOD

TECHNICAL FIELD

The present invention relates to a technique for generating a spectral image from a multi-band image.

BACKGROUND ART

A spectral image refers to an image in which each pixel is holding spectral information of an object. An RGB image developed from a spectral image excels in color reproducibility compared with an RGB image acquired by an RGB camera that is commonly used. Furthermore, a spectral image holds more information than an RGB image that is normally used. Spectral images are used in various fields, such as in the remote sensing and color design of digital cameras.

Conventionally various methods are known to acquire a spectral image of an object. One practical spectral image acquisition method that was invented estimates a spectral image from a few multi-band images using a statistical method. "Multi-band image" refers to an image group acquired by imaging an object using a plurality of optical filters each of which has a different transmission wavelength band. Hereafter an image captured in each transmission wavelength band of a multi-band image is called a "band image", and the process of capturing a multi-band image is called "multi-band imaging".

CITATION LIST

Patent Literature

[PTL1] Japanese Patent Application Laid-Open No. 2004-336657
[PTL2] Japanese Patent Application Laid-Open No. 2010-181833
[PTL3] Japanese Patent Application Laid-Open No. 2010-264276

SUMMARY OF INVENTION

Technical Problem

Depending on the object, visibility of a segment of interest may be low (that is, detailed structure of the segment of interest may be difficult to identify by visual observation) because the difference between the colors of the segment of interest and adjacent segments thereof is small. For example, in a stained pathological specimen, if a plurality of adjacent tissues are stained dark by a same pigment, the color boundary of the region is lost, and it may be difficult to check the structure of each tissue (e.g. structure inside a nucleus) by visual observation.

Patent Literature (PTL) 1 proposes a method of selecting a combination of filters to be used for capturing a spectral image such that an error between the true value and the estimated value of the spectral characteristic is minimized. By this method proposed in PTL1, however, the above mentioned color boundary loss cannot be improved, even if the spectral image estimation accuracy is high.

PTL2 proposes a method of identifying the segment of interest more clearly by extracting a portion having a distinctive wavelength characteristic for the segment of interest. However, in a region where color boundary is lost, the characteristic wavelength (color) of the segment of interest and that of the adjacent segments are the same, hence the above mentioned color boundary loss cannot be improved by the method of PTL2.

PTL3 proposes a method of detecting the subtle difference of spectral characteristics among tissues constituting a segment where color boundary is lost, by using a spectral image generated by subtracting the principal components of which contribution to the visibility of the segment of interest is high from the spectral image of the specimen, so as to improve visibility. In the case of the method of PTL3, however, the difference of spectral characteristics can be detected, but the color of the segment of interest cannot be reproduced.

With the foregoing in view, it is an object of the present invention to provide a technique for acquiring an image having high visibility with minimum color boundary loss.

Solution to Problem

The present invention in its first aspect provides an image processing apparatus generating a spectral image, comprising: an acquisition unit configured to acquire a plurality of band images which are generated by imaging an object, using a plurality of filters of which transmission center wavelengths are different from each another; a detection unit configured to select a first band image from the plurality of band images, and detect a target region that is to be improved with respect to visibility within the first band image; a selection unit configured to select a second band image, which includes information, originated from a structure of the object, within the target region, from among the plurality of band images other than the first band image; and a generation unit configured to generate a spectral image from a band image, wherein the generation unit uses at least a band image that has been captured using a same filter as the second band image, upon generating a spectral image of the object or a spectral image of another object having a same spectral characteristic as the object.

The present invention in its second aspect provides an imaging system comprising: a multi-band imaging apparatus configured to capture a band image of an object using a plurality of filters, of which transmission center wavelengths are different from each other; and the image processing apparatus according to the first aspect of the present invention, configured to acquire a plurality of band images of the object which have been captured by the multi-band imaging apparatus, and generate a spectral image.

The present invention in its third aspect provides an image processing method for generating a spectral image, comprising the steps of: acquiring a plurality of band images which are generated by imaging an object, using a plurality of filters of which transmission center wavelengths are different from each other; selecting a first band image from the plurality of band images and detecting a target region that is to be improved with respect to visibility within the first band image; selecting a second band image, which includes information, originated from a structure of the object, within the target region, from among the plurality of band images other than the first band image; and using at least a band image that has been captured using a same filter as the second band image, upon generating a spectral image of the object or a spectral image of another object having a same spectral characteristic as the object.

The present invention in its fourth aspect provides an imaging processing apparatus, comprising: an acquisition unit configured to acquire a plurality of band images which are generated by imaging an object, using a plurality of filters of which transmission center wavelengths are different from each other; a detection unit configured to select a first band image from the plurality of band images, and detect a target region that is to be improved with respect to visibility within the first band image; a selection unit configured to select a second band image which includes information, originated from the structure of the object, within the target region, from among the plurality of band images other than the first band image; and a generation unit configured to generate a display image, of which component of a band image captured using a same filter as the second band image is enhanced, based on one band image or a plurality of band images acquired by imaging the object or another object having a same spectral characteristic as the object.

The present invention in its fifth aspect provides an imaging system comprising: a multi-band imaging apparatus configured to capture a band image of an object, using a plurality of filters of which transmission center wavelengths are different from each other; and the image processing apparatus according to the fourth aspect of the present invention, configured to acquire a plurality of band images of the object which have been captured by the multi-band imaging apparatus, and generate a display image.

The present invention in its sixth aspect provides an image processing method, comprising the steps of: acquiring a plurality of band images which are generated by imaging an object, using a plurality of filters of which transmission center wavelengths are different from each other; selecting a first band image from the plurality of band images and detecting a target region that is to be improved with respect to visibility within the first band image; selecting a second band image which includes information, originated from the structure of the object, within the target region, from among the plurality of band images other than the first band image; and generating a display image, of which component of a band image captured using the same filter as the second band image is enhanced, based on one band image or a plurality of band images acquired by imaging the object or another object having a same spectral characteristic as the object.

Advantageous Effects of Invention

According to the present invention, an image having high visibility with minimal color boundary loss can be acquired.

Further features of the present invention will become apparent from the following description of exemplary embodiments with reference to the attached drawings.

BRIEF DESCRIPTION OF DRAWINGS

FIG. 1 is a diagram depicting a spectral image acquisition method according to an embodiment of the present invention.

FIG. 2A is a flow chart depicting color reproduction image development processing, and FIG. 2B is a flow chart depicting local contrast image calculation processing.

DESCRIPTION OF EMBODIMENTS

Figure 3:
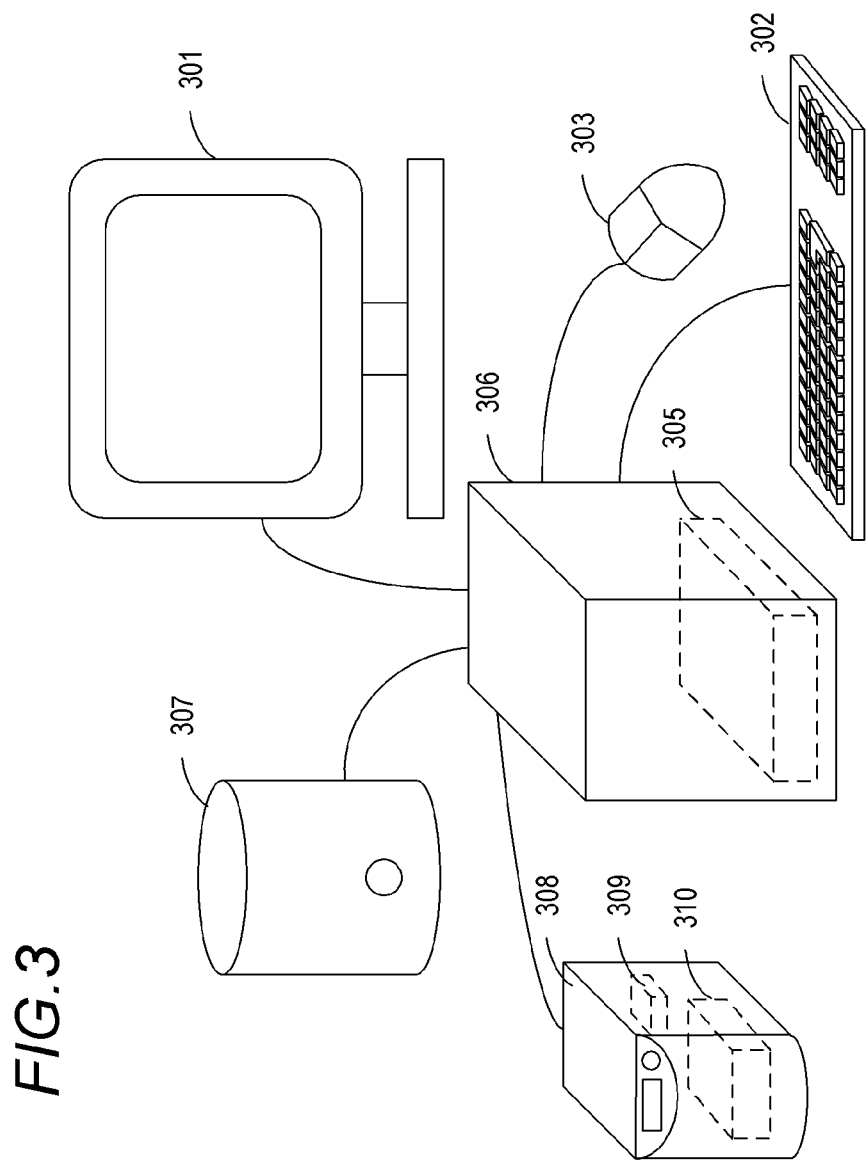
FIG. 3 is a diagram depicting a configuration of a multi-band imaging system according to Embodiment 1.

First the meaning of "spectral image", "band image", "spectral image estimation", "color reproduction image", "local contrast value" and "local contrast image", which are terms common to all the embodiments of the present invention, will be described.

A "spectral image" is image data that holds spectral characteristic data (values generated by sampling spectral radiance distribution, spectral transmittance distribution, spectral reflectance distribution or the like for each wavelength) for each pixel. For example, if the spectral characteristic data is given by an array of 50 elements (values sampled at 50 wavelengths) and a number of pixels thereof is 2000×1000, then a spectral image is expressed as a three-dimensional array of 2000×1000×50, or a 50 page image data set.

A "band image" is single color image data which is imaged via one type of color filter (or by irradiating with a color illumination light). For example, a band image is a single color specimen image, which is acquired by a monochrome camera via a narrow band filter of which central wavelength is 550 nm and transmission band width is 20 nm. In this embodiment, a number of spectral characteristic elements in a spectral image is greater than a number of band images (a number of color filters or a number of narrow band filters). A plurality of band images are normally called a "multi-band image". In this embodiment, it is defined that a multi-band image is different from a spectral image because the number of elements is different therebetween.

A "spectral image estimation" is a method of acquiring spectral image data from a plurality of band image data of which number is less than a number of elements of the spectral characteristics. In spectral image estimation, a matrix to correspond the pixel values of the band images and the spectral characteristic of the spectral image is calculated, using such a statistical method as the principal component analysis or the Wiener estimation. Hereafter, this matrix is called "spectral estimation matrix". An expression to calculate the spectral estimation matrix using the principal component analysis is given by Expression 1, as described in detail in PTL1.

[Math. 1]

$$r = Dv$$

$$D = B(FB)^{-1}$$

$$F = TES \qquad \text{(Expression 1)}$$

Here r denotes a spectral transmittance vector of the specimen at an arbitrary pixel point of the spectral image, D denotes a spectral estimation matrix, and v denotes a pixel value vector at the same pixel point of the multi-band image. B denotes a matrix of which column vector is the plurality of principal components, T denotes a matrix of which column vector is the transmittance of the filter, E denotes a spectral radiance distribution vector of the light source, and S denotes a total spectral sensitivity of the imaging system.

Instead of the method using the principal component analysis, the spectral estimation matrix may be calculated by the Wiener estimation.

A "color reproduction image" is a color image that has same colorimetric values as the spectral image on the display device. The color space of the color reproduction image is arbitrary, but an RGB image is used in this embodiment.

A processing of developing (generating) a color reproduction image from a spectral image will be described with reference to the flow chart in FIG. 2A. The processing in FIG. 2A is a processing executed by an image processing apparatus, which is constituted by a computer, an image processor or the like.

In step S101 (XYZ conversion), the image processing apparatus converts the spectral characteristic of each pixel of the spectral image into XYZ tristimulus values. The conversion formula is given by Expression 2, for example.

[Math. 2]

$$\begin{pmatrix} X \\ Y \\ Z \end{pmatrix} = \begin{pmatrix} Erx' \\ Ery' \\ Erz' \end{pmatrix} \quad \text{(Expression 2)}$$

Here X, Y and Z denote the XYZ tristimulus values, and x, y and z denote the color-matching function vectors of x, y and z ("'" on the upper right side indicates a transposed vector).

In step S102 (RGB conversion), the image processing apparatus converts XYZ tristimulus values into the RGB values of the display device. If the color space of the display device is sRGB, the conversion formula is given by Expression 3, for example.

[Math. 3]

$$\begin{pmatrix} R \\ G \\ B \end{pmatrix} = L_0 \times M^{-1} \times \begin{pmatrix} X \\ Y \\ Z \end{pmatrix} \quad \text{(Expression 3)}$$

$$M^{-1} = \begin{pmatrix} 3.2406 & -1.5372 & -0.4986 \\ -0.9689 & 1.8758 & 0.0415 \\ 0.0557 & -0.2040 & 1.0570 \end{pmatrix}$$

$L_0$ denotes brightness (cd/m$^2$) of the monitor. The conversion of the XYZ tristimulus values into the RGB values of the display device may be performed by creating an LUT (LookUp Table) or an approximate conversion formula in advance.

In step S103, the image processing apparatus determines whether the RGB conversion S102 was performed for all the pixels. The XYZ conversion S101 and the RGB conversion S102 are repeatedly executed until no unprocessed pixels remain. The color reproduction is developed (generated) from the spectral image by the above steps.

A "local contrast value" is a local contrast value in the vicinity area of each pixel of the band image. A "local contrast image" is image data of which size is the same as the band image data, and has a "local contrast value" as a pixel value.

The processing flow to calculate the local contrast image data from the band image data will be described with reference to the flow chart in FIG. 2B. The processing in FIG. 2B is also a processing executed by the image processing apparatus.

In step S201 (initialization), as a memory space to hold the local contrast image data, the image processing apparatus secures a two-dimensional array having a same image size as the band image size. All the elements of the array are initialized to zero.

In step S202 (local contrast value calculation), the image processing apparatus determines a local contrast value of each pixel of the band image data, and assigns the calculated value to the array element corresponding to each pixel.

For example, a method of setting a range of 3×3 pixels, centering the pixel of interest (j, k) as a range of calculating the local contrast values, and determining the array element at index (j, k) of the local contrast image data using a known Michelson contrast formula, will be described. First the image processing apparatus determines a maximum value Lmax and a minimum value Lmin in the range of 3×3 pixels, where the pixels (j−1, k−1) and (j+1, k+1) of the band image data are at opposite angles. The value c, the Michelson contrast, is given by Expression 4.

[Math. 4]

$$c = \frac{L_{max} - L_{min}}{L_{max} + L_{min}} \quad \text{(Expression 4)}$$

By Expression 4, the local contrast value (pixel value of local contrast image data) corresponding to the pixel of interest (j, k) is determined. Here the local contrast value is calculated based on the local range of 3×3 pixels centering around the pixel of interest, but the size and shape of the local range may be freely set depending on the specimen type, the size of the tissue and the like.

In step S203, the image processing apparatus determines whether the local contrast value was calculated for all the pixels. The local contrast value calculation S203 is repeatedly executed until no unprocessed pixels remain.

In step S204 (local contrast image normalization), the image processing apparatus standardizes the local contrast image such that the minimum value becomes 0 and the maximum value becomes 255 in the local contrast image. The range of 0 to 255 is an example based on the assumption that each pixel of the local contrast image is displayed as 8-bits data. In the case of 16-bit data, the local contrast image could be normalized such that the minimum value becomes 0 and the maximum value becomes 65535. In this way, normalization corresponding to the quantization bit rate of the pixel can be performed.

The above processing is executed for a plurality of band image data included in the multi-band image data respectively, and a plurality of local contrast images, corresponding to the plurality of band images respectively, are acquired.

The spectral image acquisition method according to an embodiment of the present invention will be described with reference to FIG. 1. FIG. 1 is schematic diagrams depicting examples of the specimen, the band images, the local contrast images, the spectral image, and the color reproduction image.

For example, in a specimen 10 stained with HE (hematoxylin and eosin), hematoxylin colors the nucleus bluish-purple, and eosin colors the cytoplasm pink. Depending on the stained state of the specimen, the entire nucleus may be stained dark bluish-purple, so in some cases it may become difficult to visually recognize the internal structure of the nucleus due to color boundary loss if a standard optical microscope is used. Images 11 to 13 are band images that have different wavelength regions, which were acquired by imaging the specimen 10 using a plurality of narrow band filters of which transmittance center wavelengths are different. The band image 11 is an image captured by a filter of which transmission center wavelength is 400 nm, the band image 12 is an image captured by a filter of which transmission center wavelength is 530 nm, and the band image 13 is an image captured by a filter of which transmission center wavelength is 700 nm. Acquired images are different depending on the wavelength region.

Images 14 to 16 are local contrast images generated from the band images 11 to 13 respectively by the processing in FIG. 2B. The brightness of the local contrast image (level of the local contrast value) indicates the amount of information that originated from the structure of the specimen 10 included in the band image (hereafter this information is called "structure information"). In other words, a bright region in the local contrast image (a region of which local contrast value is high) indicates that the structure information is included in the same region of the band image. On the other hand, a dark region in the local contrast image (region of which local contrast value is low) indicates that little structure information is included in the same region of the band image. For example, in the case of the local contrast image 15 captured by the 530 nm filter, the local contrast value is high at the contour of the nucleus (boundary of the nucleus and the cytoplasm), and the local contrast value is low in the other portions (inside the nucleus and the cytoplasm). This means that the band image 12 captured by the 530 nm filter includes the structure information of the contour of the nucleus, but includes little information on the internal structure of the nucleus and the cytoplasm. In the case of the local contrast image 16 captured by the 700 nm filter, on the other hand, the local contrast value is high in both the contour of the nucleus and inside the nucleus. This means that the band image 13 captured by the 700 nm filter includes not only information on the contour of the nucleus, but also information on the structure inside the nucleus. As this example shows, a band image in the wavelength band that is different from the absorption peak wavelength of the specimen 10 (that is, the absorption peak wavelength of the staining pigment) may be more suitable to acquire the structure information of the specimen.

Therefore in the embodiment of the present invention, when a spectral image of the specimen 10 is generated (by spectral image estimation), at least the band image 13, which includes the structure information in the region where visibility has dropped due to color boundary loss (that is, the region to be improved with respect to visibility) is used. In concrete terms, the information of the band image 13 is used as one element of the vector v of Expression 1, which is used for the spectral image estimation. Thereby, the spectral image 17 that includes maximum information on the internal structure of the nucleus can be acquired. As a result, the structure information included in the band image 13 can be effectively reflected on the color reproduction image 18, which is developed (generated) from the spectral image 17, and the color reproduction image 18 having high visibility, with minimizing the color boundary loss inside the nucleus, can be acquired.

In this embodiment, the "local contrast value" is used to detect a region to be improved with respect to visibility and to evaluate whether structure information is present, but any index may be used if the index shows the dispersion of pixel values in a plurality of pixels in a vicinity area of each pixel. For the index which can show this dispersion of pixel values, a value determined by another contrast calculation method, a variance of the pixel values, an edge intensity or the like, can be used.

<Embodiment 1>

Hue, at which visibility is dropped due to color boundary loss, differs depending on the staining type (type of pigments to be used). Hue, at which visibility is dropped also differs depending on the specimen type (e.g. type of organ), since color development (how specimen is stained) differs depending on the specimen. Therefore the band region (filter) of the band image that is used for generating the spectral image should be selected appropriately according to the staining type and/or the specimen type.

In Embodiment 1 of the present invention, prior to actual imaging of the specimen, an appropriate combination of filters is selected using a test target, which has the same spectral characteristic as the specimen. Then multi-band imaging of the specimen is performed using the selected combination of filters, and the spectral image is generated based on the acquired plurality of band images, whereby the color reproduction image is generated. As a result, the color reproduction image, of which color boundary loss has been improved and visibility has been improved, can be displayed to the user. Furthermore, the same combination of filters can be used for specimens if the staining type/specimen type is the same, hence the filter selection processing using the test target can be performed only once when a staining type/specimen type specimen is new.

A multi-band imaging system equipped with the image processing apparatus according to an embodiment of the present invention will be described with reference to FIG. 3.

The multi-band imaging system has a display device 301, a keyboard 302, a mouse 303, a storage device 305, a computer 306, an image server 307, a multi-band imaging apparatus 308, imaging filters 309 and a test target 310. The storage device 305 is integrated into the computer 306. In this embodiment, the computer 306 functions as the image processing apparatus for performing various image processing operations, by executing the required programs. All or a part of the functions of the image processing apparatus may be performed by an ASIC (Application Specific Integrated Circuit) or may be performed by the image server 307 or the multi-band imaging apparatus 308. Further, an image processor, such as a GPU (Graphics Processing Unit), may be integrated into the computer 306.

The display device 301, the keyboard 302, the mouse 303, the image server 307, the multi-band imaging apparatus 308 and the computer 306 are connected via general purpose I/F cables. The image server 307 and the computer 306 are connected via a LAN, but may be connected via another type of network.

The display device 301 is a display device using liquid crystals, EL (Electro-Luminescence), CRT (Cathode Ray Tube) or the like. This display device 301 is used for displaying a band image, a spectral image and a color reproduction image of a specimen. A staining type selection GUI (Graphical User Interface) is displayed on the display device 301 by an image processing program which is executed by the computer 306. Details on the GUI will be described later. The keyboard 302 or the mouse 303 is used for instruction operation for the staining type selection GUI.

The storage device 305 is a storage medium which non-temporarily stores the OS and programs executed by the computer 306, and various parameters are accessed by the OS and programs, image data and the like. For the storage device 305, a magnetic disk drive, such as an HDD (Hard Disk Drive) or a semiconductor device, such as an SSD (Solid State Disk) is used.

The storage device 305 stores, for example, spectral radiance distribution data of the light source, which is required for later mentioned spectral estimation matrix calculation, optical characteristic data of the multi-band imaging apparatus 308, spectral transmittance data of the narrow band filter, and imaging parameters such as exposure time. The storage device 305 also stores data sets of the names of all the test targets stored in the multi-band imaging apparatus 308 and the peak wavelengths of the staining pigments of these test targets, and xyz color-matching function data that is used for the color reproduction image calculation processing in FIG. 2A.

The image server 307 is a computer that can save image data and perform various processing operations separate from the computer 306.

The multi-band imaging apparatus 308 captures an enlarged image of a pathological specimen, and acquires and stores it as high resolution digital pathological image data. This apparatus 308 is called a WSI (Whole Slide Imaging) apparatus, a digital microscope or the like. To perform multi-band imaging of the specimen, the multi-band imaging apparatus 308 of this embodiment includes m number of narrow band imaging filters 309, so as to cover at least the wavelength band of visible light (e.g. 380 to 780 nm). The number of filters (m) is arbitrary, but about a dozen to several tens of imaging filters 309 can be included.

The staining type selection GUI will be described with reference to FIG. 4. The staining type selection GUI is a GUI for the user to specify a staining type and specimen type to be used for a test target. The staining type selection GUI 401 has a list 402 of the test targets, a radio button 404 used for selecting a test target, and a start button 405. In the list 402, the staining type, the specimen type and the absorption wavelength of staining pigments are displayed for each test target. If a plurality of absorption peak wavelengths exist, the plurality of peak wavelengths are displayed. If the test target is determined only by the staining type, a specimen type name is not displayed. In the same manner, if the test target is determined only by specimen type, a staining type name is not displayed. When the user operates a pointer 403 by the keyboard 302 or the mouse 303, specifies a radio button 404 of the test target to be used, and presses the start button 405, the selection of the test target is completed.

Figure 5:
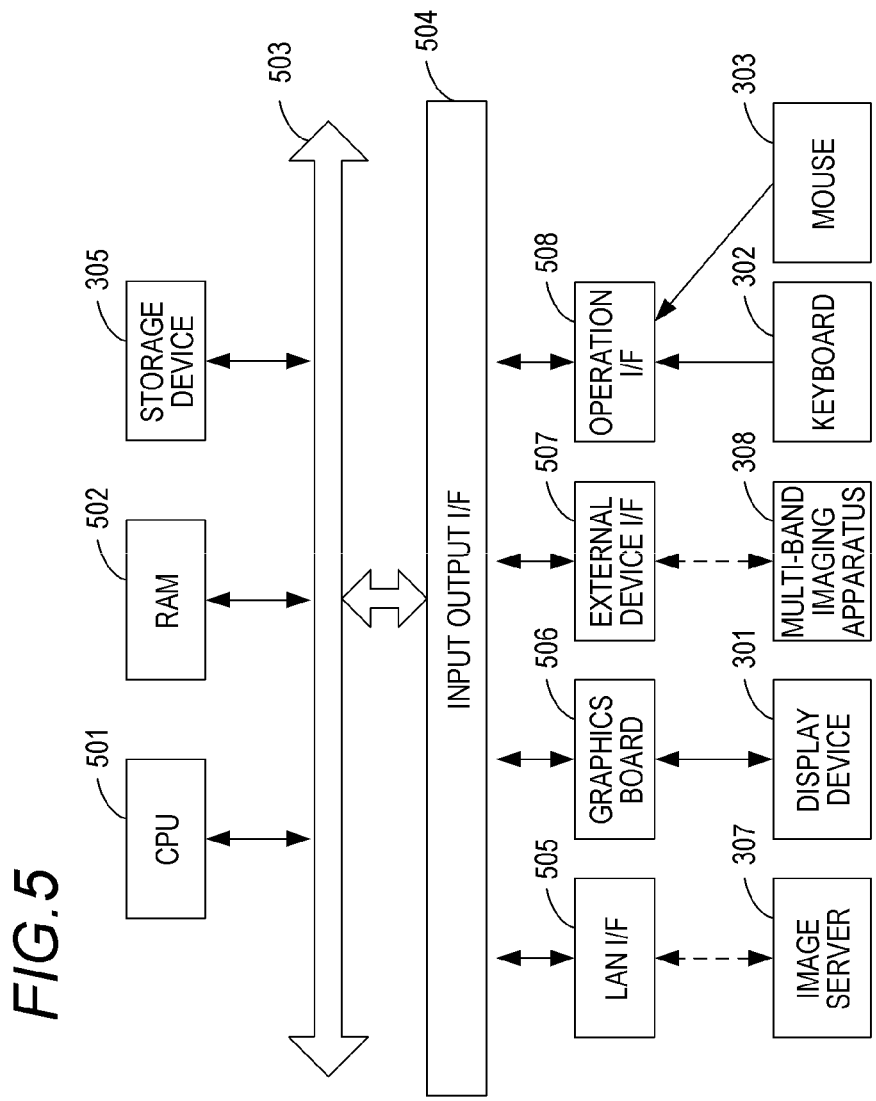
FIG. 5 is a block diagram depicting hardware of a computer according to Embodiment 1.

Now the hardware configuration of the computer 306 will be described with reference to the block diagram in FIG. 5. The computer 306 has a CPU (Central Processing Unit) 501, a RAM (Random Access Memory) 502, a storage device 305, a data input/output I/F 504, and an internal bus 503 that interconnects these composing elements. The CPU 501 accesses the RAM 502 and the like when necessary, and systematically controls each block of the computer 306 while performing various data processing operations. The RAM 502 is used as a work area of the CPU 501, and temporarily stores the OS and various programs during executing, and various data, such as band image data to be processed and filter transmission wavelength data. To the data input/output I/F 504, the image server 307 is connected via a LAN I/F 505, the display device 301 is connected via a graphics board 506, and the multi-band imaging apparatus 308 is connected via an external device I/F 507. Instead of the storage device 305, the above mentioned various data may be stored in the image server 307 or in the multi-band imaging apparatus 308. Furthermore, the keyboard 302 and the mouse 303 are connected to the data input/output I/F 504 via an operation I/F 508.

It is assumed that the display device 301 is connected as an external device, but a computer integrated with the display device may be used. A notebook PC is an example of this integrated unit. For the input device, a pointing device, such as the keyboard 302 and the mouse 303, is assumed to be used, but a touch panel may be used. In this case, the touch panel may be integrated with the display device 301.

In the above configuration, the computer 306 executes the multi-band imaging software (programs) and controls the necessary hardware resources, whereby the image processing apparatus and the image processing method, according to the embodiment of the present invention, are implemented.

Figure 6:
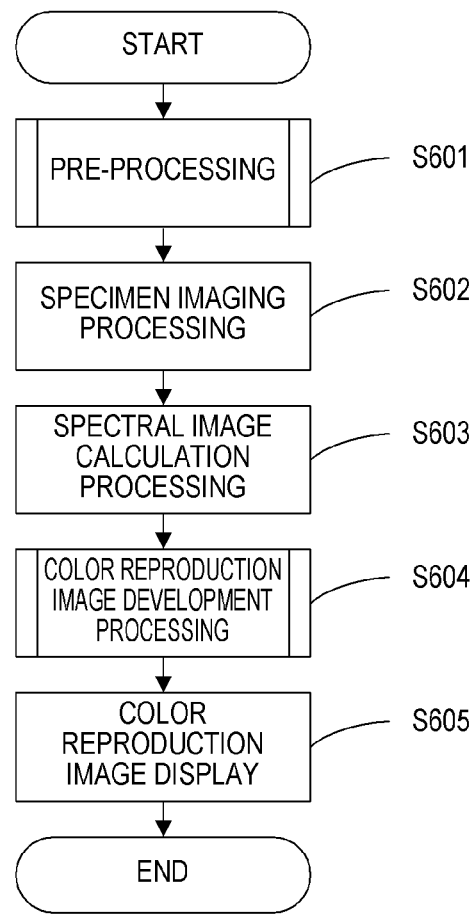
FIG. 6 is a flow chart depicting the multi-band imaging system according to Embodiment 1.

A general processing flow of this embodiment will be described with reference to the flow chart in FIG. 6. The processing in FIG. 6 is executed by the computer 306 (image processing apparatus).

In step S601 (pre-processing), the image processing apparatus selects a filter to be used for the multi-band imaging, and calculates the spectral estimation matrix. Details on the flow of the pre-processing (S601) will be described with reference to the flow chart in FIG. 7.

Figure 4:
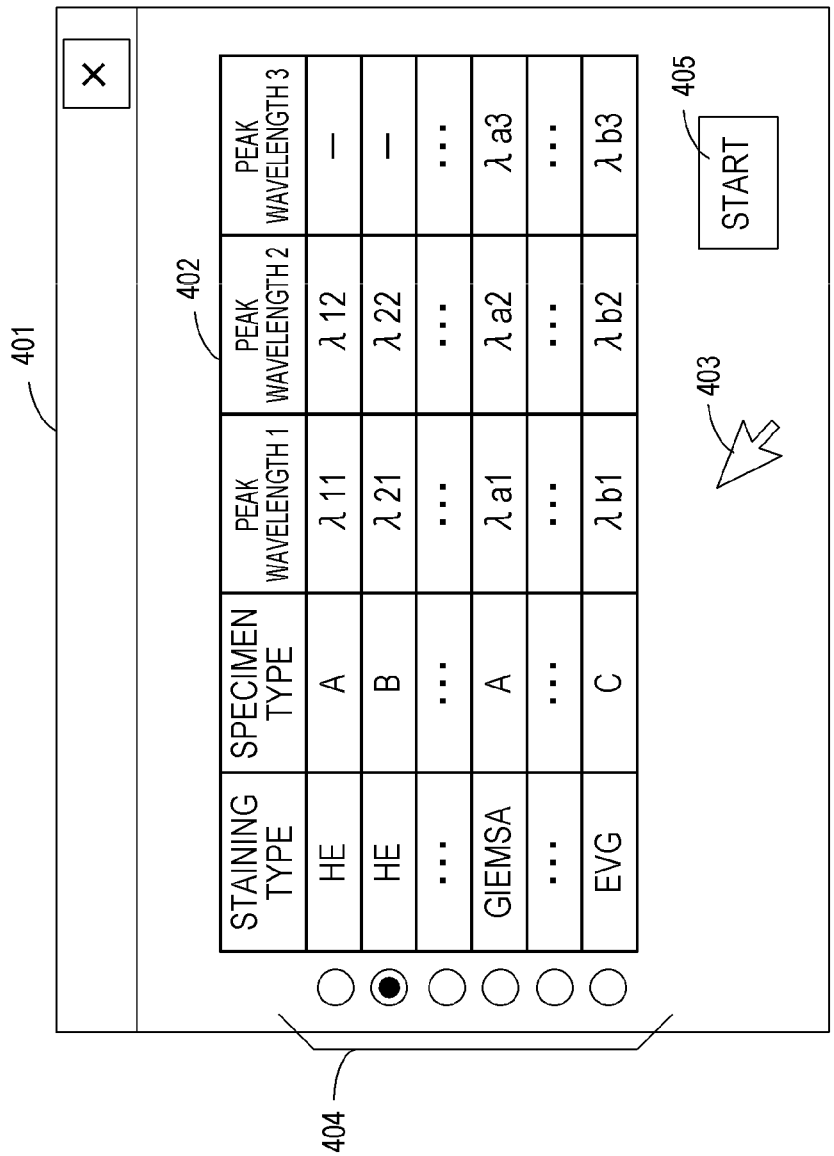
FIG. 4 shows a GUI (Graphical User Interface) screen display example according to Embodiment 1.

In step S701 (test target selection), the image processing apparatus displays the staining type selection GUI in FIG. 4 on the display device 301, and prompts the user to specify a test target. When the user selects a test target having the same staining type and specimen type as the specimen to be imaged, using a mouse 303 or the like, this information is loaded into the image processing apparatus. In this embodiment, the test target is selected, but a part of the specimen to be imaged may be used as the test target.

In step S702 (test target imaging), the image processing apparatus reads the exposure time data of each filter from the storage device 305, and forwards the exposure time data and the information on the test target selected in step S701 to the multi-band imaging apparatus 308. Based on this information, the multi-band imaging apparatus 308 performs multi-band imaging of the test target 310 using m number of internal imaging filters 309. The acquired multi-band image data (data on m number of band images) is loaded into the image processing apparatus. If the multi-band imaging has been executed for the same test target 310, and if this multi-band image data can be acquired from the storage device 305 or the image server 307, then the processing in step S702 may be skipped.

In step S703 (reference spectral image calculation), the image processing apparatus calculates the spectral image data of the test target from the acquired multi-band image data and the spectral radiance distribution data of the light source read from the storage device 305. The method of calculating the spectral image data from a large volume of band image data acquired by narrow band filters is well known. For example, from a pixel value (brightness value) of a band image, which was acquired using a filter of which transmission center wavelength is a and the spectral radiance of wavelength a in the spectral radiance distribution of the light source, the spectral radiance of this pixel with respect to wavelength a can be determined. By calculating this for a pixel at the same location of m number of band images respectively, the spectral radiance can be discretely determined for m number of wavelengths. Then by calculating the spectral radiance among the m number of wavelengths by linear interpolation or curve interpolation, the spectral radiance distribution of this one pixel can be acquired. The spectral image data can be acquired by performing this processing for all the pixels in the image.

In this embodiment, the spectral image data is acquired by the above mentioned method since narrow band filters are used, but the spectral image data may be generated by the spectral estimation method of Expression 1, if the principal components or the spectral estimation matrix of the test target have been stored in the storage device 305 in advance. In this case, not only the narrow band filters, but also the broad band filters may be used for the imaging filters 309 in the multi-band imaging apparatus 308. The spectral image calculated in step S703 is hereafter called a "reference spectral image".

In step S704 (reference color reproduction image development processing), the image processing apparatus generates a color reproduction image from the reference spectral image. This processing flow is the same as the color reproduction image calculation processing in FIG. 2A. In the XYZ conversion (step S101), the image processing apparatus reads the color-matching function stored in the storage device 305 and uses this function. Hereafter the color reproduction image calculated in step S704 is called a "reference color reproduction image".

In step S705 (principal component calculation), the image processing apparatus analyzes the principal components using the spectral characteristics of a plurality of pixel points of the reference spectral image as samples. Then the image processing apparatus selects p (m≥p) types of principal components having a high contribution rate, out of the determined principal components. In this embodiment, principal component analysis is used, but any method may be used if the spectral characteristic can be expressed by the linear combination with the principal component, such as the singular value decomposition.

In step S706 (local contrast image calculation), the image processing apparatus calculates a local contrast image from the band image acquired in step S702. This processing flow is the same as the local contrast image calculation processing in FIG. 2B. The image processing apparatus repeats the processing in step S706 until the local contrast image is generated for all the m number of band images (step S707).

In step S708 (comparison target band image selection), the image processing apparatus reads the absorption peak wavelength of the test target (staining type, specimen type) selected in step S701 from the storage device 305. Then the image processing apparatus selects a band image corresponding to the absorption peak wavelength. Here "band image corresponding to the absorption peak wavelength" refers to a band image captured with a filter of which transmission center wavelength is the same as or closest to the absorption peak wavelength. Hereafter the band image corresponding to the absorption peak wavelength, which is selected in step S708, is called a "comparison target band image", and a local contrast image of the comparison target band image is called a "comparison target local contrast image". The comparison target band image of this embodiment corresponds to the "first band image" of the present invention.

In this embodiment, the information on the absorption peak wavelength is acquired from the storage device 305, but the user may input the value of the absorption peak wavelength (or transmission center wavelength). Alternately, the image processing apparatus may determine the contrast value of the entire image for each of the m number of images, and select a band image of which contrast value is highest as the comparison target band image. For example, the contrast value of the entire image may be a total value or a mean value of the local contrast values of the entire image. The comparison target band image may be selected by any method, such as selecting a band image having a predetermined wavelength for the comparison target band image, or the user may specify the comparison target band image.

In step S709 (low contrast region extraction), the processing to detect the "target region to be improved with respect to visibility" in the comparison target band image is performed. In concrete terms, using the comparison target local contrast image, the image processing apparatus detects a low contrast region in the comparison target local contrast image as the "target region to be improved with respect to visibility". Here "low contrast region" refers to a region of which local contrast value is a threshold or less. For example, if the image 15 in FIG. 1 is the comparison target local contrast image, then the low contrast region is a region indicated by the black pixels in the image 15, which includes internal regions of the nucleus where visibility drops due to color boundary loss. The threshold is a value that is set in advance to extract a low contrast region, and can be set to an arbitrary value. The threshold may be set for each predetermined number of bits of the local contrast image or for each type of test target, and the user may set this threshold using a GUI or the like. If a region of which local contrast value is the threshold or more is surrounded by low contrast regions in the comparison target contrast image, then this region may be included in the low contrast regions.

In step S710 (local contrast RMS calculation), the image processing apparatus determines an RMS value of the local contrast value in a region corresponding to the low contrast region, for each one of (m−1) number of local contrast images other than the comparison target local contrast image. The RMS value is a root mean square. Although an RMS value is used in this embodiment, other statistical values, such as a mean value or a maximum value, may be used instead.

In step S711 (high contrast filter selection), a processing to select a band image, which includes the structure information in the target region to be improved with respect to visibility, out of the band image group other than the comparison target band image, is performed. In concrete terms, the image processing apparatus selects a local contrast image of which RMS value is highest, out of the (m−1) number of local contrast images other than the comparison target local contrast image. The RMS value indicates a level of the local contrast value in a region corresponding to a low contrast region, in other words, the RMS value indicates an amount of structure information included in the corresponding region of the band image. Therefore, if a band image corresponding to the local contrast image of which RMS value is highest (hereafter called "high contrast band image") is used, the structure information in the low contrast region, which is lost in the comparison target band image, can be reproduced. The image processing apparatus selects the filter 209 used for capturing the high contrast band image (hereafter called "high contrast filter") as one of the filters to be used for multi-band imaging of the specimen. In the case of FIG. 1, for example, the RMS value of the image 16, in which the contrast inside the nucleus is displayed, is the highest, hence the band image 13 is selected as the high contrast band image, and the 700 nm filter is selected as the high contrast filter. The high contrast band image of this embodiment corresponds to the "second band image" of the present invention.

If the test target has a plurality of absorption peak lengths (number of absorption peak wavelengths q>1), the image processing apparatus repeats the processing operations in step S708 to S711 for each absorption peak wavelength (step S712). If the high contrast filter is a filter which has already been selected in step S711, a filter of which RMS value is second highest can be selected. By the above processing, at least q number of filters are selected.

The relationship of a number of absorption peak wavelengths (q), a total number of filters in the multi-band imaging apparatus (m), a number of filters used for the multi-band imaging of the specimen (n), and a number of factors used for calculating the spectral estimation matrix (p) is m≥n≥p>q. It is preferable that the number of filters to be used (n) is as few as possible since multi-band imaging takes a lengthy processing time. In this embodiment, the multi-band imaging apparatus 308 includes a dozen to several tens of filters 209, but it is assumed that only 5 to 10 filters 209 are used for the multi-band imaging of a specimen.

In step S713 (other filter selection), the image processing apparatus selects the remaining filters to be used for the multi-band imaging of the specimen. The number of remaining filters is (n−q) since q number of filters were selected in step S712. For the method of selecting filters, the method disclosed in PTL2, for example, can be used. In concrete terms, the image processing apparatus creates a set of n number of filters by combining the already selected q number of filters and the arbitrarily selected (n−q) number of filters. The image processing apparatus calculates the spectral estimation matrix and the spectral image by Expression 1, using the n number of band images which correspond to the n number of filters, and calculates the color reproduction image from the spectral image by the processing in FIG. 2A. Then the image processing apparatus compares the calculated color reproduction image and the reference color reproduction image which was generated from the m number of band images in step S704, and evaluates the difference between the two color reproduction images. For the evaluation value, a statistical value (e.g. total value, mean value, maximum value) of the color difference between a part or all of the pixels of the images may be used. The image processing apparatus performs the above processing for each of the candidates of a combination of n number of filters respectively, and selects a combination of the filters by which the difference of the color reproduction images is smallest, as the n number of filters to be used for the multi-band imaging of the specimen.

In this embodiment, the color difference between the color reproduction images is selected for the evaluation value, but the spectral residual between the spectral image determined from the n number of band images and the reference spectral image may be used as the evaluation value. An alternative is that a threshold may be set for the color difference, so that a combination of filters of which color difference is the threshold or less and of which spectral residual is smallest is selected. Another alternative is that a combination of filters, of which color difference is the threshold or less and which includes the highest number of filters having a high RMS value (calculated in step S710), may be selected.

To shorten the calculation time, filters of which transmission center wavelengths are the same as or close to the absorption peak wavelength of the specimen or the peak wavelength of the light source may be selected as the remaining filters other than the q number of filters selected in step S711. An alternative is that filters of which transmission center wavelength are the same as or close to the wavelength corresponding to the principal component of the spectral distribution of the specimen (or the test target) acquired in step S705 may be selected. Here "close to the absorption peak wavelength" refers to transmission center wavelengths that are within a range where the spectral characteristic, that is substantially the same as the spectral characteristic at the absorption peak wavelength, can be acquired. The band of a filter has some margin, therefore if the transmission center wavelength of the filter is within a predetermined range (e.g. ±30 nm) from the absorption peak wavelength, then it is expected that a substantially same spectral characteristic as the filter of which transmission center wavelength is exactly the absorption peak wavelength can be acquired. This also applies to the phrases "close to the peak wavelength of the light source" and "close to the wavelength corresponding to the principal component". Out of the filters included in the predetermined range, one or a plurality of filters may be selected sequentially from the filter of which transmission center wavelength is closest to the absorption peak wavelength or the like, or a filter, with which the above mentioned color difference or the spectral residual becomes small, may be selected.

In step S714 (spectral estimation matrix calculation), the image processing apparatus calculates a spectral estimation matrix D by Expression 1, based on: the principal component of the specimen calculated in step S705; the transmission characteristics of selected n number of filters; the spectral radiance distribution of the light source; and the optical characteristics of the multi-band imaging apparatus. The data of the transmission characteristics of the filters, the data of the spectral radiance distribution data of the light source, the data of the optical characteristics of the multi-band imaging apparatus and the like are read from the storage device 305.

By the above steps, n number of filters to be used for the multi-band imaging of the specimen and the spectral estimation matrix D are determined. This information is stored in the storage device 305. Then processing advances to step S602 in FIG. 6.

In step S602 (specimen imaging processing), the image processing apparatus controls the multi-band imaging apparatus 308 and performs multi-band imaging of the specimen by the selected n number of filters. The acquired data of the multi-band image (n number of band images) is loaded into the image processing apparatus.

In step S603 (spectral image calculation processing), the image processing apparatus calculates the spectral image of the specimen according to Expression 1, based on the acquired multi-band image and the spectral estimation matrix D calculated in the pre-processing (step S601). In this processing, the pixel values of each filter may be multiplied by a predetermined value so that arbitrary wavelength components are strengthened or weakened. For example, the pixel values of a band image acquired using the filter selected in step S711 (high contrast filter selection) may be multiplied by a constant that is greater than 1, so that the degree of contribution of this band image to the spectral image can be increased.

In step S604 (color reproduction image development processing), the image processing apparatus converts the spectral image into the color reproduction image to be displayed on the display device 301. This processing flow is the same as the color reproduction image development processing shown in FIG. 2A. In the XYZ conversion (step S101), the image processing apparatus reads the color-matching function stored in the storage device 305, and uses this function.

In step S605 (color reproduction image display), the image processing apparatus displays the color reproduction image generated in step S604 on the display device 301.

According to the configuration of this embodiment described above, a region of which visibility may drop due to color boundary loss can be automatically detected using the multi-band image data of the test target. Further, a filter for the multi-band imaging is automatically selected so as to improve the visibility of this region, hence a spectral image, with which a color reproduction image having improved visibility with less color boundary loss, can be acquired, compared with the case of observation using a standard optical microscope.

In the experiment using an HE stained specimen, it is confirmed that a band image corresponding to the absorption peak wavelength of eosin is selected as the comparison target band image, and the local contrast RMS becomes the maximum in a band image that was captured by a filter of which transmission center wavelength is 700 nm. It was also confirmed that when a spectral image is generated from n number of band images including this band image of 700 nm, and a color reproduction image is generated from this spectral image, the visibility of the inside of the nucleus, of which structure was not recognized by visual observation, improved.

<Embodiment 2>

A multi-band imaging system equipped with an image processing apparatus according to Embodiment 2 of the present invention will now be described.

In Embodiment 1, a region of which visibility is not good is detected in the local contrast image, a filter to improve the visibility of this region is selected based on the local contrast RMS value determined from this region, and a color reproduction image, in which visibility of the specimen has been improved, is displayed for the user. According to the method of Embodiment 1, a region having array element values that are the threshold value or more (a region other than low contrast regions) in the comparison target local contrast image is not determined as a region where color boundary loss is generated.

A characteristic of Embodiment 2 is that the user specifies a region to be improved with respect to visibility. As a result, a spectral image, from which a color reproduction image with higher visibility can be generated, can be acquired for the region specified by the user.

The system configuration of the multi-band imaging system is the same as the configuration of Embodiment 1, but a difference from Embodiment 1 is that the image processing program displays a region specification GUI on the display device 301, in addition to the staining type selection GUI.

The region specification GUI will be described with reference to FIG. 8. The region specification GUI 801 includes a region 802 where a specimen image 803 is displayed, and a determination button 806. By operating a pointer 804 using a keyboard or a mouse (e.g. by dragging the mouse), the user can specify a partial area 805 to improve visibility in the specimen image 803. When the specification ends, the region specification is completed by clicking on the determination button 806. This function corresponds to the "region specification unit" of the present invention.

Figure 9:
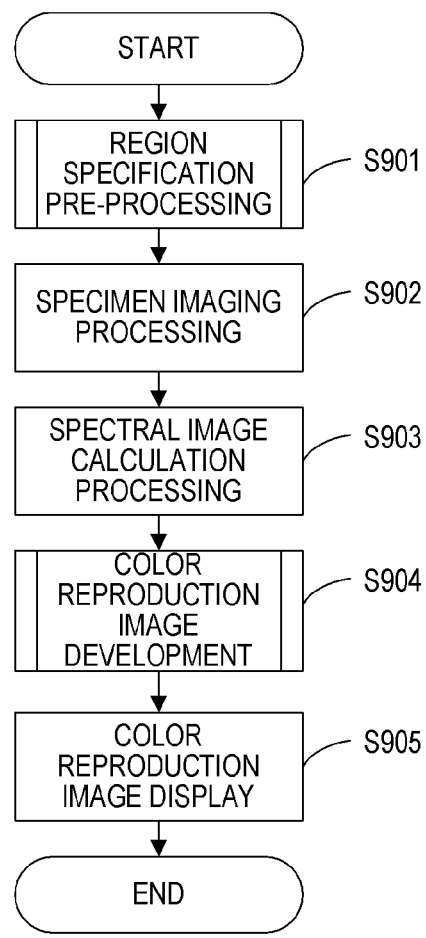
FIG. 9 is a flow chart depicting a multi-band imaging system according to Embodiment 2.

A general processing flow of this embodiment will be described with reference to the flow chart in FIG. 9. The processing in FIG. 9 is executed by the computer 306 (image processing apparatus).

Figure 10:
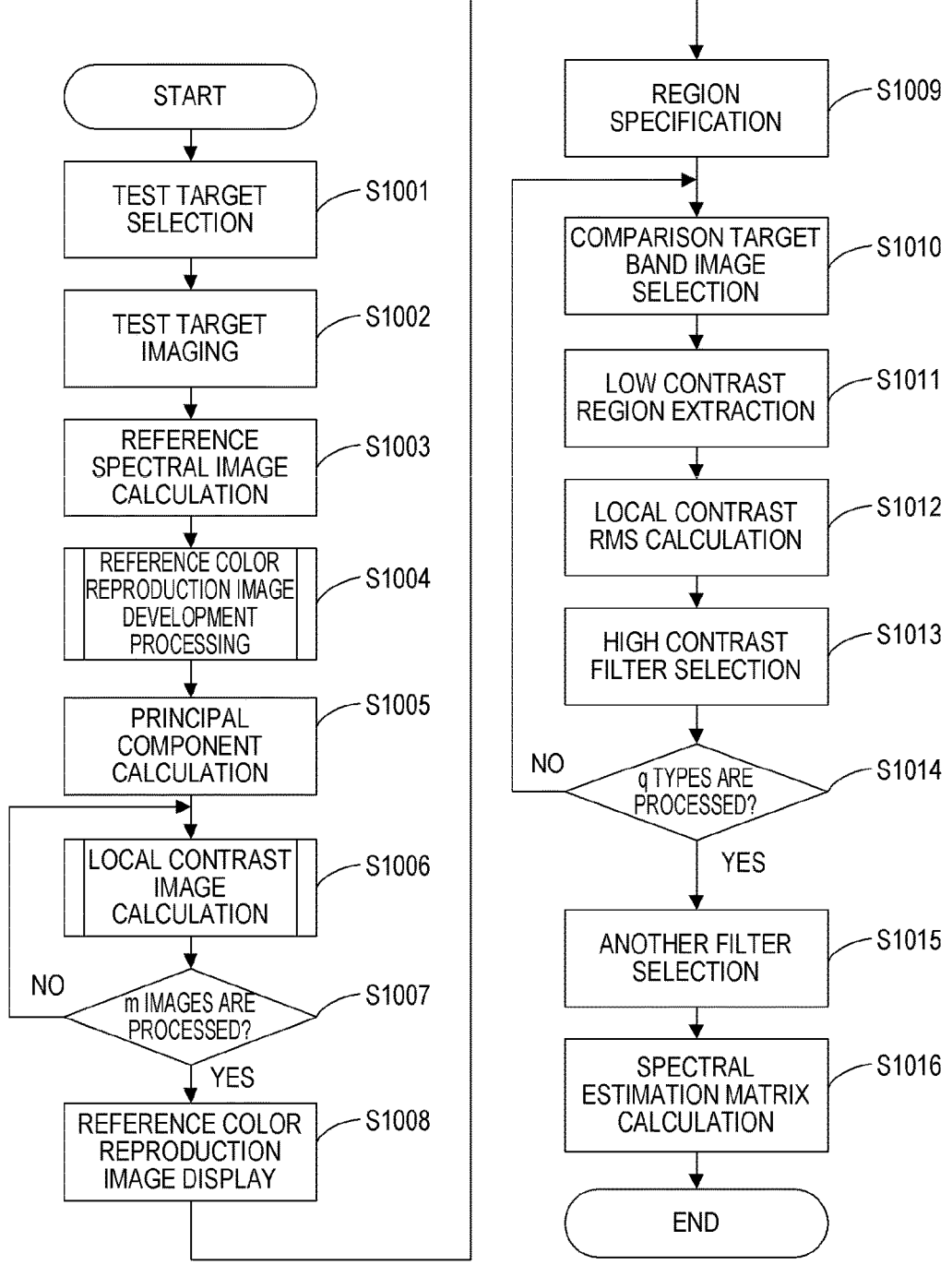
FIG. 10 is a flow chart depicting pre-processing according to Embodiment 2.

In step S901 (region specification pre-processing), the image processing apparatus selects a filter to be used for imaging, and calculates the spectral estimation matrix. The processing flow of the region specification pre-processing (S901) will be described with reference to the flow chart in FIG. 10.

Figure 7:
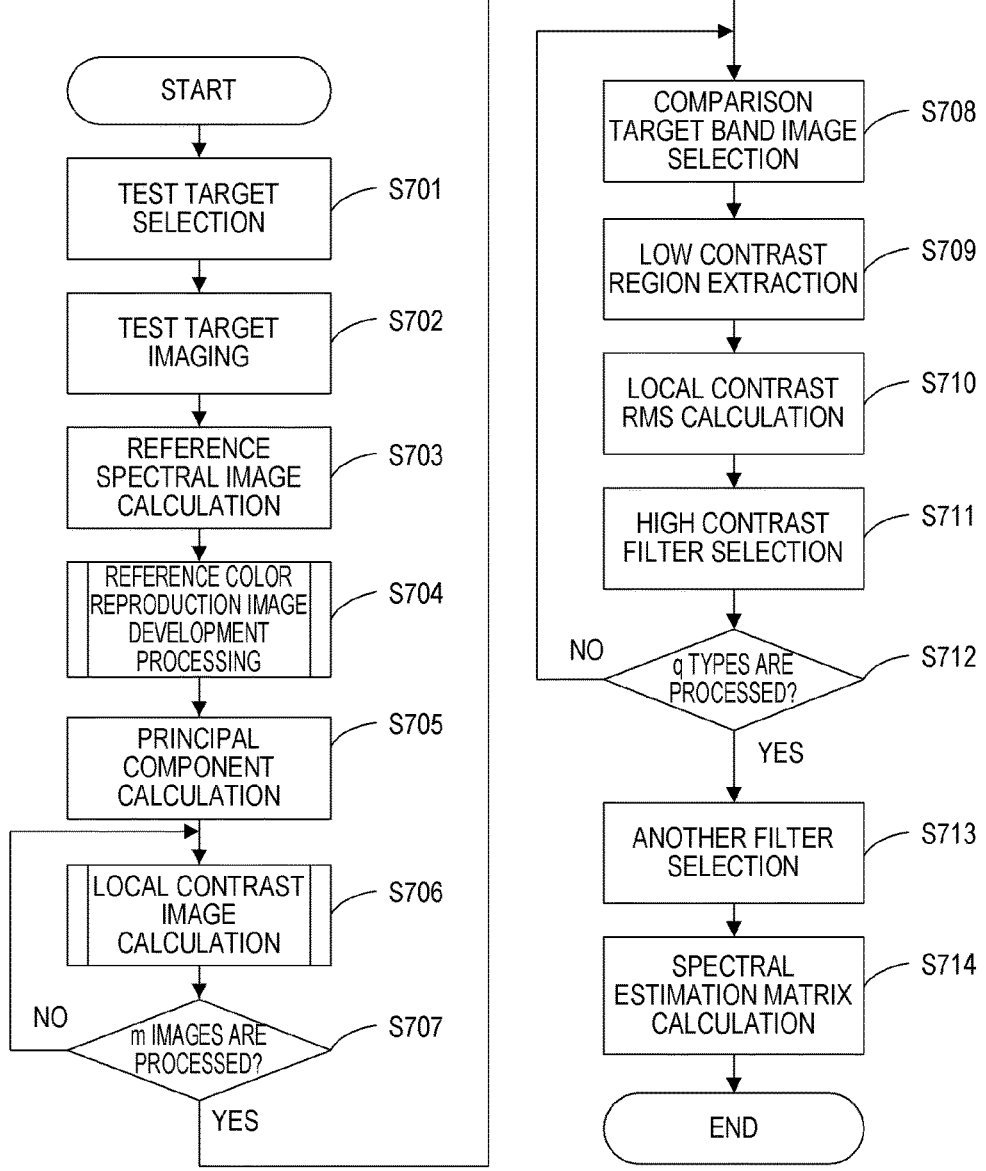
FIG. 7 is a flow chart depicting pre-processing according to Embodiment 1.

The processing operations in steps S1001, S1002, S1003, S1004, S1005, S1006 and S1007 are the same processing operations as steps S701, S702, S703, S704, S705, S706 and S707 in FIG. 7.

Figure 8:
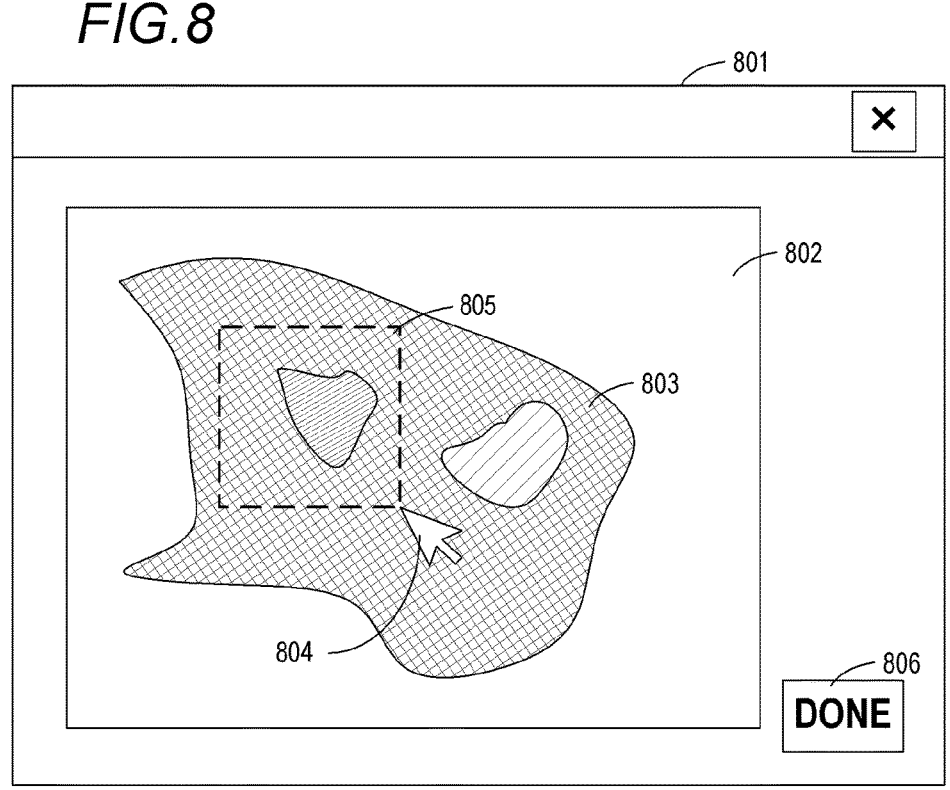
FIG. 8 shows a GUI screen display example according to Embodiment 2.

In step S1008 (reference color reproduction image display), the image processing apparatus displays the region specification GUI 801 in FIG. 8 on the display device 301, and displays a reference color reproduction image in the region 802. In this embodiment, the reference color reproduction image is displayed on the region specification GUI 801, but if imaging was performed with a plurality of broadband filters in step S1002, an RGB image may be calculated from the plurality of band image data using a standard RGB image acquisition method, and this RGB image may be displayed.

In step S1009 (region specification), the image processing apparatus prompts the user to specify a region. When the user specifies the region to be improved with respect to visibility using the keyboard 302 or the mouse 303, the information thereof is loaded into the image processing apparatus. Hereafter the region specified in this step is called the "specified region".

Processing in step S1010 is the same as step S708 in FIG. 7. In step S1009 (low contrast region extraction), the image processing apparatus again normalizes the local contrast values within the specified region of the comparison target contrast image, so that the minimum value becomes 0 and the maximum value becomes 255. Then the image processing apparatus extracts a region of which local contrast value is the threshold or less from the specified region, as a low contrast region. The range of the normalization may be changed according to a number of bits of the local contrast image, just like step S203. The threshold is an arbitrary value that is set in advance to extract a low contrast region, just like step S709 in FIG. 7.

The processing operations in the subsequent steps S1012, S1013, S1014, S1015 and S1016 are the same as step S710, S711, S712, S713 and S714 in FIG. 7. By the above steps, n number of filters to be used for the multi-band imaging of the specimen and the spectral estimation matrix D are determined. This information is stored in the storage device 305. Then processing advances to step S902 in FIG. 9. The processing operations in steps S902, S903 and S904 are the same as steps S602, S603 and S604 in FIG. 6. In step S905, the image processing apparatus displays the color reproduction image, in which visibility of the region specified in step S1009 has been improved, on the display device 301.

According to the above mentioned configuration of this embodiment, filters for multi-band imaging are automatically selected such that the visibility of a region which the user specified on the test target improves. Further, a spectral image, with which a color reproduction image having improved visibility with less color boundary loss, can be acquired, compared with the case of observation using a standard optical microscope.

<Embodiment 3>

A multi-band imaging system equipped with an image processing apparatus according to Embodiment 3 of the present invention will now be described.

In Embodiment 1 and Embodiment 2, the multi-band imaging of the test target is performed before imaging the specimen, whereby a combination of filters to improve visibility is selected, and a corresponding spectral estimation matrix is calculated. In Embodiment 3, on the other hand, a color reproduction image, in which visibility of segments with color boundary loss has been improved, is developed from an already captured multi-band image of the specimen.

The system configuration of the multi-band imaging system according to this embodiment is essentially the same as the configuration of Embodiment 1, therefore description thereof is omitted.

Figure 11:
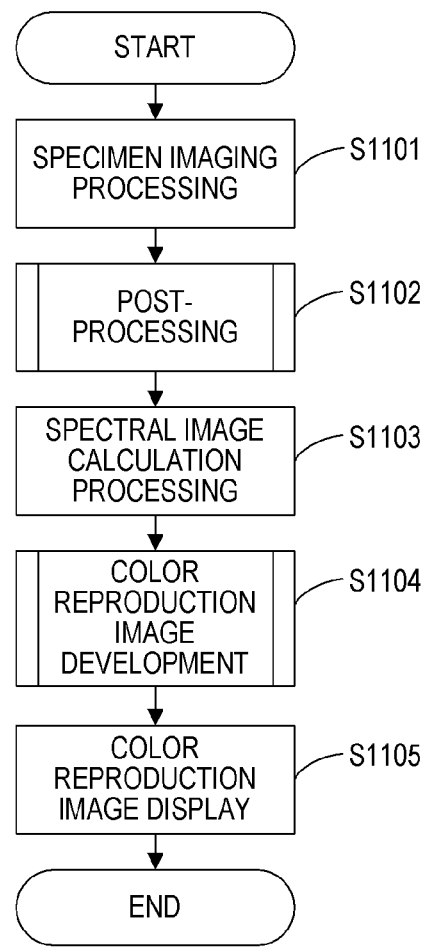
FIG. 11 is a flow chart depicting a multi-band imaging system according to Embodiment 3.

A processing flow of this embodiment will be described with reference to the flow chart in FIG. 11. The processing in FIG. 11 is executed by the computer 306 (image processing apparatus).

In step S1101 (specimen imaging), the image processing apparatus controls the multi-band imaging apparatus 308, and performs multi-band imaging for the specimen using all the m number of filters. Although the multi-band imaging is performed in this embodiment, the multi-band image data of the specimen may be acquired from the image server 307 or the storage device 305.

Figure 12:
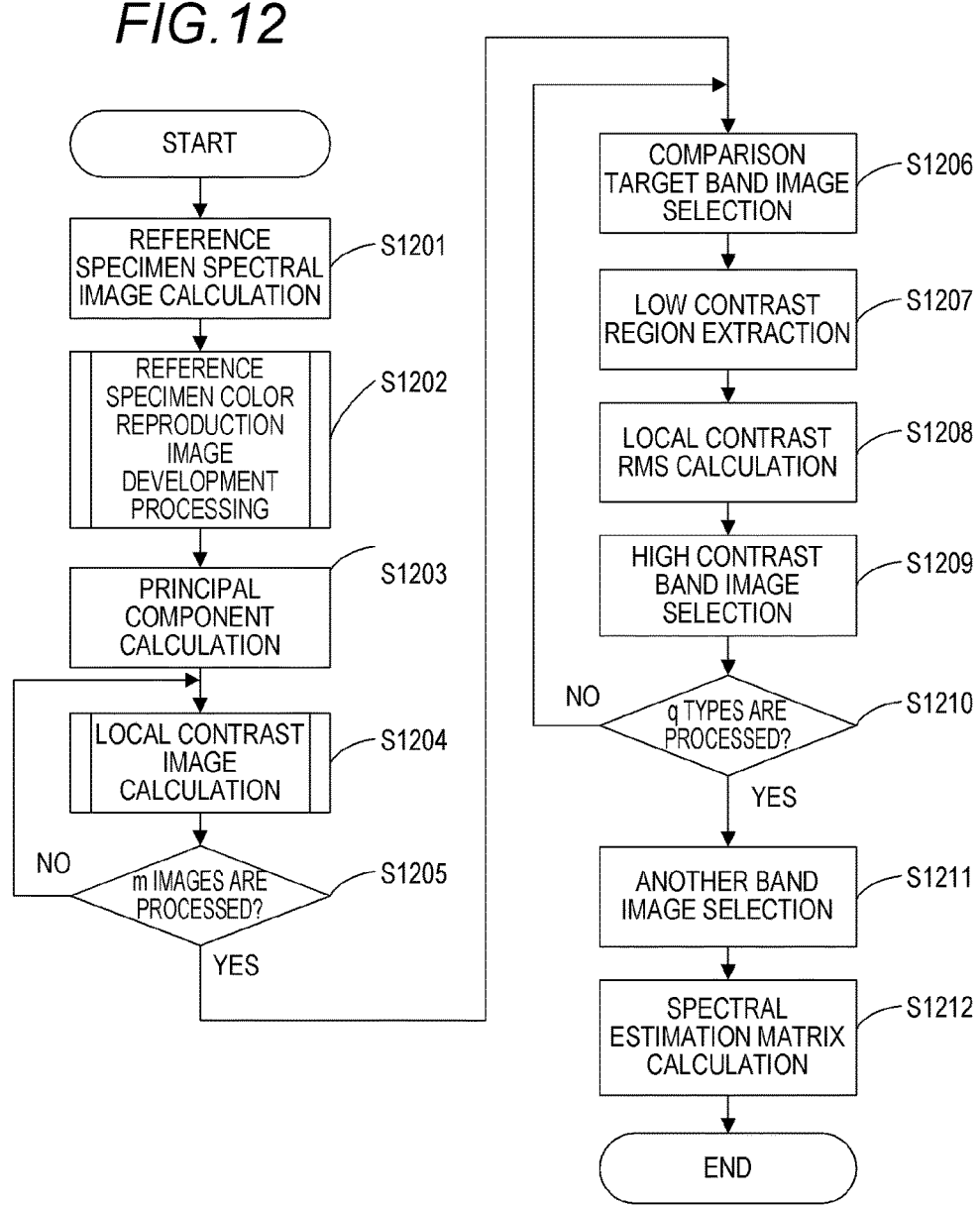
FIG. 12 is a flow chart depicting post-processing according to Embodiment 3.

In step S1102 (post-processing), the image processing apparatus selects a combination of band image, and calculates the spectral estimation matrix to develop a color reproduction image in which visibility of segments with color boundary loss has been improved. The processing flow in step S1102 will be described with reference to the flow chart in FIG. 12.

In step S1201 (reference specimen spectral image calculation), the image processing apparatus generates a spectral image of the entire specimen from the acquired multi-band image of the specimen. In step S1202 (reference color reproduction image development processing), the image processing apparatus generates a color reproduction from the spectral image generated in step S1201. The processing flow in steps S1201 and S1202 is the same as steps S704 and S705 in FIG. 7.

The processing operations in steps S1203 to S1212 are essentially the same as steps S705 to S714 in FIG. 7. The only difference, however, is that filters to be used for imaging the specimen are selected in steps S711 and S713 in FIG. 7, whereas band images to be used for calculating the spectral image are selected in steps S1209 and S1211 in FIG. 12.

By the above steps, band images to be used for calculating the spectral image of the specimen and the spectral estimation matrix are determined. This information is stored in the storage device 305. Then processing advances to step S1103 in FIG. 11. The processing operations in steps S1103, S1104 and S1105 are the same as steps S603, S604 and S605 in FIG. 6.

According to the configuration of this embodiment described above, a combination of band images to improve visibility can be automatically selected from the already acquired multi-band image of the specimen. Therefore there is no need to re-capture a multi-band image to acquire a spectral image in which visibility has been improved. Further, a spectral image, in which visibility has been improved, can be generated without the specimen, only if the multi-band image data is available. Furthermore, if a plurality of multi-band images are captured in advance, band images can be freely selected according to the target to improve visibility. Another advantage of this embodiment over Embodiments 1 and 2 is that the time to acquire the color reproduction image is shorter and user convenience is heightened.

<Embodiment 4>

An image processing apparatus to generate an image in which segments, where visibility is not good, has been more visible, according to Embodiment 4 of the present invention, will be described.

In Embodiment 1 to Embodiment 3, the multi-band imaging is performed using filters (high contrast filters) that can acquire band images which include a large amount of structure information within the target region, whereby a spectral image, in which visibility of the target region has been improved, is generated from a plurality of band images. In Embodiment 4, the imaging is performed using the selected filters, just like Embodiments 1 to 3, but a spectral image is not generated, and the display image (observation image), in which visibility of the target region has been improved, is directly generated from the band images. The configuration of the image processing apparatus according to this embodiment is the same as Embodiment 1.

Figure 13:
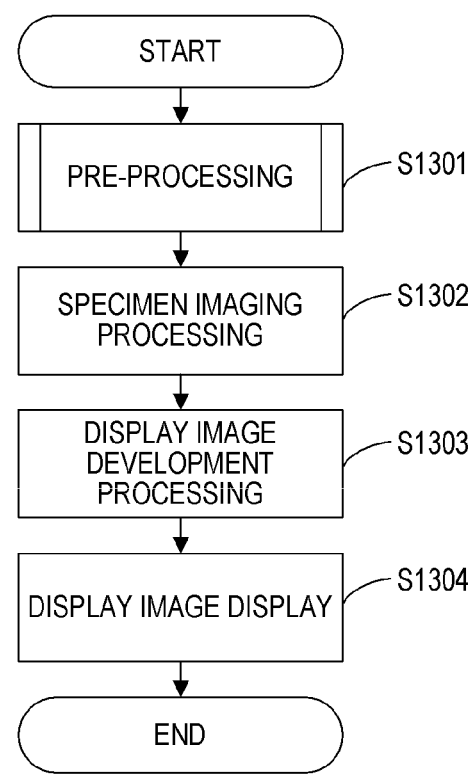
FIG. 13 is a flow chart depicting a multi-band imaging system according to Embodiment 4.
Figure 14:
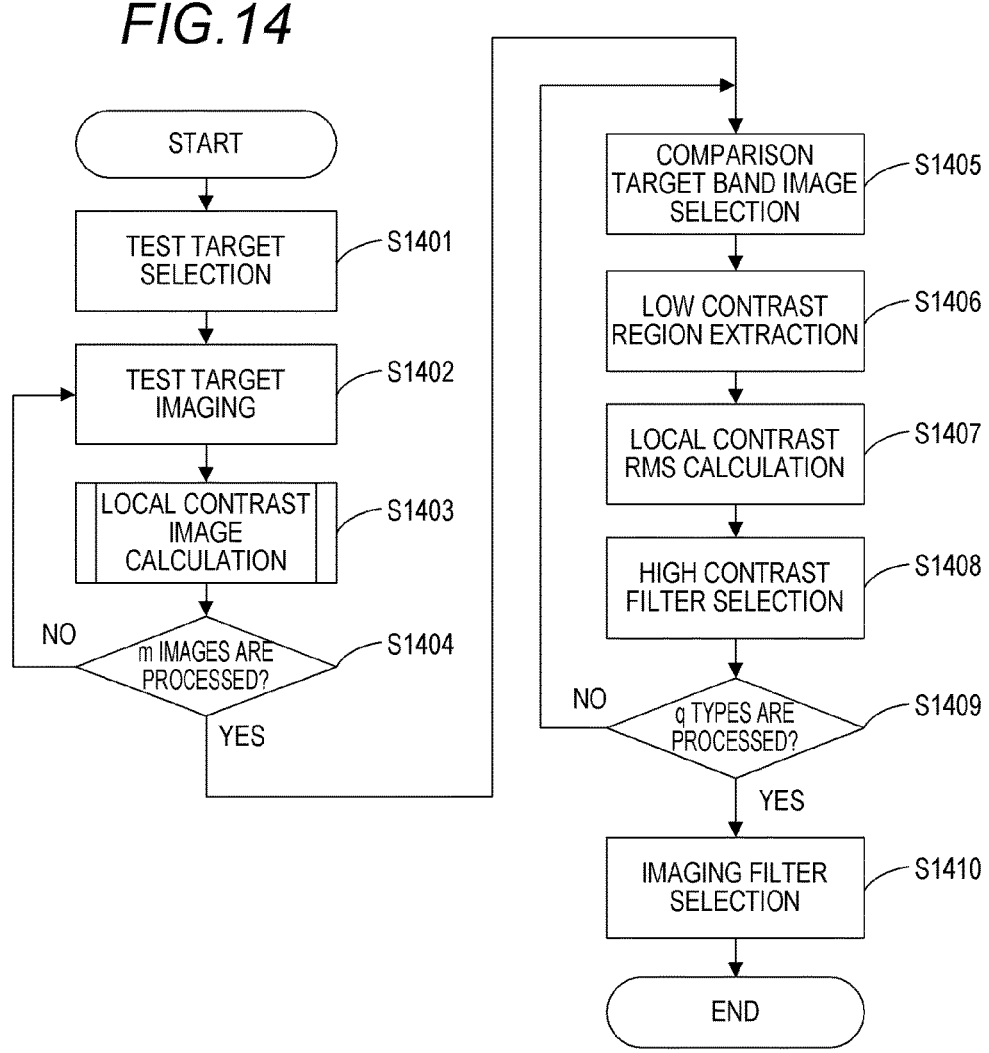
FIG. 14 is a flow chart depicting post-processing according to Embodiment 4.

A processing flow of this embodiment will be described with reference to the flow chart in FIG. 13. The processing in FIG. 13 is executed by the computer 306 (image processing apparatus). In step S1301 (pre-processing), the image processing apparatus selects the filters to be used for the multi-band imaging. Details on the flow of the pre-processing (S1301) will be described with reference to the flow chart in FIG. 14.

Steps S1401 and S1402 are the same as steps S701 and S702 in FIG. 7, and steps S1403 to S1409 are the same as steps S708 to S712 in FIG. 7.

In step S1410 (imaging filter selection), the image processing apparatus selects filters to be used for imaging if necessary, besides the filters selected in step S1408.

In step S1302 (specimen imaging processing), the image processing apparatus performs the imaging processing for the specimen using the selected filter or a plurality of filters.

In step S1303 (display image development processing), the image processing apparatus develops (generates) a display image to be displayed on the display device 301, from the captured band image or a plurality of band images. At this time, the image processing apparatus develops (generates) the display image such that the components of the band image(s) acquired using the filters selected in step S1408 (high contrast filter selection) is/are enhanced.

For example, if there is one band image that was captured, the display image may be developed (generated) according to the specification of the display device 301, regarding this band image as a monochrome image or a pseud-color image. If there is a plurality of band image data, the brightness and color of the components of a band image acquired by the filter selected in step S1408, out of the color images developed from the plurality of band images, may be enhanced. For example, in the band image acquired by the filter selected in step S1408, a color of the region of which pixel value is the threshold or less, may be replaced with a predetermined color, and this color image may be used as the display image.

In step S1304 (display image display), the image processing apparatus displays the display image developed in step S1303, just like step S605 (color reproduction image display).

According to the configuration of this embodiment described above, a segment of which visibility may drop by color boundary loss can be automatically detected using the multi-band image of the test target. Further, a filter, with which image data to improve visibility of the region can be developed, is automatically selected, whereby an image in which visibility of the segment has improved can be displayed.

In this embodiment as well, the user may specify a region to be improved with respect to visibility on the image data of the test target, after multi-band imaging of the test target is performed, as in the case of Embodiment 2. Further, a combination of band images, by which a display image to improve the visibility can be calculated, may be automatically selected from the already acquired multi-band image of the specimen, as in the case of Embodiment 3.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-104609, filed on May 22, 2015 and Japanese Patent Application No. 2015-249613, filed on Dec. 22, 2015, which are hereby incorporated by reference herein in their entireties.

REFERENCE SIGNS

10: specimen
11 to 12: band images
14 to 15: local contrast images
17: spectral image
18: color reproduction image
306: computer (image processing apparatus)
308: multi-band imaging apparatus

The invention claimed is:

1. An image processing apparatus generating spectral image data, the image processing apparatus comprising:
   an acquisition unit configured to acquire a plurality of band images which are obtained by imaging an object with a respective plurality of filters of which transmission center wavelengths are different from each other;
   a first selection unit configured to select a target region in a first band image of the plurality of band images;
   a second selection unit configured to select a second band image from among the plurality of band images, the second band image including more information on a structure inside the target region than the first band image, and to determine, as a filter to be used, a filter which has been used for obtaining the second band image; and
   a generation unit configured to generate spectral image data comprising spectral characteristic elements from band images,
   wherein a number of the band images is less than a number of the spectral characteristic elements, and
   wherein the generation unit uses at least a band image obtained with the filter to be used for generating spectral image data of the object or spectral image data of another object having a same spectral characteristic as the object.

2. The image processing apparatus according to claim 1, further comprising a calculation unit configured to calculate, for each pixel of each band image, an index indicating dispersion of pixel values of a plurality of pixels in a vicinity area of each of the pixels,
   wherein the first selection unit selects the target region in the first band image, based on the index.

3. The image processing apparatus according to claim 2, further comprising a region specification unit configured to display an image of the object on a display device and allow a user to specify a partial region in the displayed image,
   wherein the first selection unit detects, as the target region, a region which is inside the partial region of the first band image and which has the index that is smaller than a threshold.

4. The image processing apparatus according to claim 2, wherein the second selection unit selects, as the second band image, a band image of which statistical value of the index in the target region is greater than the first band image.

5. The image processing apparatus according to claim 2, wherein the second selection unit selects, as the second band image, a band image of which statistical value of the index in the target region is greatest.

6. The image processing apparatus according to claim 4, wherein the statistical value is an RMS value, a mean value, or a maximum value.

7. The image processing apparatus according to claim 2, wherein the index is a local contrast value in the vicinity area.

8. The image processing apparatus according to claim 1, wherein the first selection unit selects, as the first band image, a band image that corresponds to an absorption peak wavelength of the object.

9. The image processing apparatus according to claim 1, wherein, upon generating spectral image data of the object or spectral image data of another object having a same spectral characteristic as the object, the generation unit uses at least:
   a band image obtained with the filter to be used; and
   a band image obtained with a filter which has a transmission center wavelength in a predetermined range of which a center is one of (i) an absorption peak wavelength of the object, (ii) a peak wavelength of a light source used for obtaining the band image, and (iii) a wavelength corresponding to a principal component of a spectral distribution of the object.

10. The image processing apparatus according to claim 1, wherein the object is a pathological specimen.

11. An imaging system comprising:
   a multi-band imaging apparatus configured to obtain a band image of an object using a plurality of filters, of which transmission center wavelengths are different from each other; and
   the image processing apparatus according to claim 1, configured to acquire a plurality of band images of the object by the multi-band imaging apparatus, and to generate a spectral image data.

12. An image processing method for generating spectral image data, the image processing method comprising the steps of:
   acquiring a plurality of band images which are obtained by imaging an object with a respective plurality of filters of which transmission center wavelengths are different from each other;
   selecting a target region in a first band image of the plurality of band images;
   selecting a second band image from among the plurality of band images, the second band image including more information on a structure inside the target region than the first band image;
   determining, as a filter to be used, a filter which has been used for obtaining the second band image; and
   generating spectral image data comprising spectral characteristic elements from band images, wherein a number of the band images is less than a number of the spectral characteristic elements; and wherein at least a band image obtained with the filter to be used is used for generating spectral image data of the object or spectral image data of another object having a same spectral characteristic as the object.

13. An imaging processing apparatus comprising:

an acquisition unit configured to acquire a plurality of band images which are obtained by imaging an object with a respective plurality of filters of which transmission center wavelengths are different from each other;

a first selection unit configured to select a target region in a first band image of the plurality of band images;

a second selection unit configured to select a second band image, from among the plurality of band images the second band image including more information on a structure inside the target region than the first band image, and to determine, as a filter to be used, a filter which has been used for obtaining the second band image; and a generation unit configured to generate a display image, of which a component of a band image obtained with the filter to be used is enhanced, based on one band image or a plurality of band images acquired by imaging the object or another object having a same spectral characteristic as the object.

14. An imaging system comprising:

a multi-band imaging apparatus configured to obtain a band image of an object, using a plurality of filters of which transmission center wavelengths are different from each other; and the image processing apparatus according to claim 13, configured to acquire a plurality of band images of the object by the multi-band imaging apparatus, and to generate a display image.

15. An image processing method comprising the steps of:

acquiring a plurality of band images which are obtained by imaging an object with a respective plurality of filters of which transmission center wavelengths are different from each other;

selecting a target region in a first band image of the plurality of band images;

selecting a second band image from among the plurality of band images, the second band image including more information on a structure inside the target region than the first band image;

determining, as a filter to be used, a filter which has been used for obtaining the second band image; and generating a display image, of which a component of a band image obtained with the filter to be used is enhanced, based on one band image or a plurality of band images acquired by imaging the object or another object having a same spectral characteristic as the object.

* * * * *